United States Patent [19]

Mallozzi et al.

[11] 4,317,994

[45] Mar. 2, 1982

[54] LASER EXAFS

[75] Inventors: Philip J. Mallozzi, Delaware; Harold M. Epstein; Robert E. Schwerzel, both of Columbus; Bernerd E. Campbell, Upper Arlington, all of Ohio

[73] Assignee: Battelle Memorial Institute, Columbus, Ohio

[21] Appl. No.: 105,816

[22] Filed: Dec. 20, 1979

[51] Int. Cl.$^3$ ............................................. G01N 23/20
[52] U.S. Cl. ........................................ 250/275; 250/272; 250/493
[58] Field of Search ............... 250/493, 272, 273, 275, 250/274

[56] References Cited

U.S. PATENT DOCUMENTS

| | | | |
|---|---|---|---|
| 2,835,820 | 5/1958 | Birks | 250/275 |
| 2,842,670 | 7/1958 | Birks | 250/275 |
| 4,058,486 | 11/1977 | Mallozzi et al. | 250/493 |
| 4,134,012 | 1/1979 | Smallbone et al. | 250/272 |
| 4,206,364 | 6/1980 | Dixon et al. | 250/493 |

Primary Examiner—Bruce C. Anderson

Attorney, Agent, or Firm—Philip M. Dunson

[57] ABSTRACT

Apparatus (10) for obtaining EXAFS data of a material (11). A lens (12) directs a pulse of radiant energy (13) from a laser (14) onto a metal target (15) to produce X-rays (16) of a selected spectrum and intensity at the target (15). A baffle (17) directs X-rays (16) from the target (15) onto a spectral dispersive monochromator (18) which directs the spectrally resolved X-rays (16R) therefrom onto a photographic film 20. A film of material (11) is located in the path (22) of only a portion (16L) of the X-rays (16) throughout a selected spectral band, and the resolved X-rays (16R) directed onto the photographic film (20) form two separate images thereon comprising a reference spectrum (26R) representative of a portion of the X-rays (16U) throughout the selected band that was not affected by the film of material (11) and an absorption spectrum (26A) representative of a portion of the X-rays (16L) throughout the selected band that was modified by transmission through the film of material (11). The laser pulse (13) typically has a width of less than about 10 nanoseconds, and the material (11) may be in a highly transient state.

20 Claims, 5 Drawing Figures

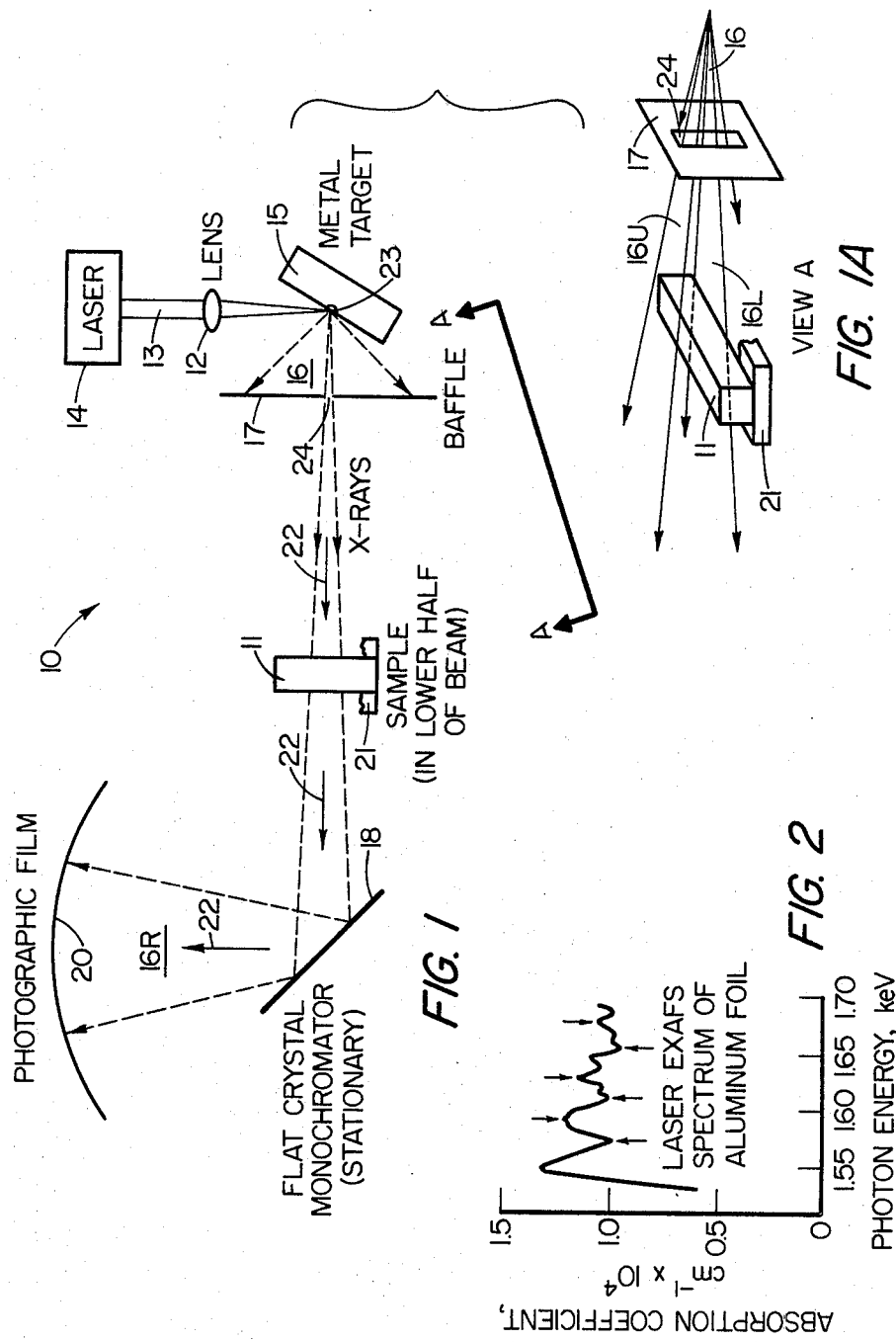

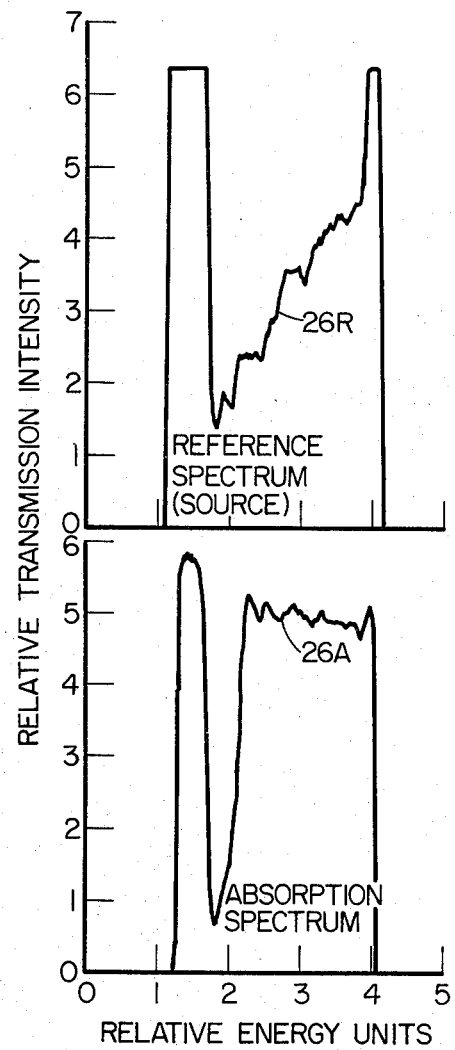
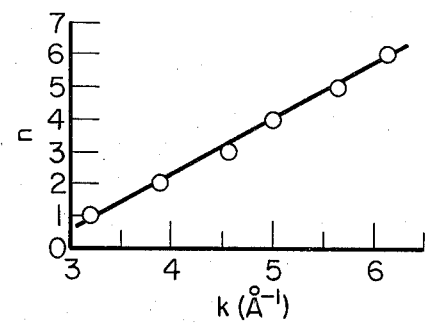
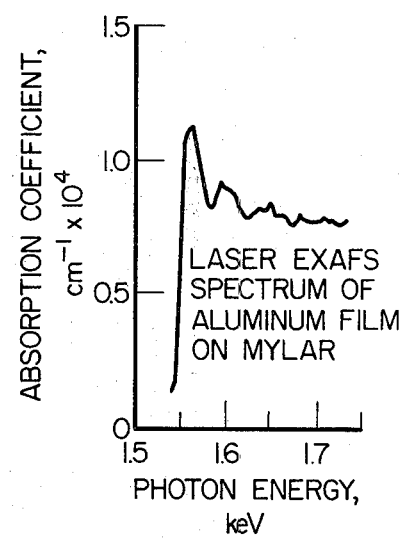
FIG. 4
FIG. 3
FIG. 5

LASER EXAFS

The Government of the United States has rights in this invention pursuant to Grant AFOSR-78-3575 awarded by the U.S. Air Force Office of Scientific Research.

FIELD

This invention relates to laser EXAFS, and especially to fast EXAFS spectroscopy with a single pulse of laser-produced x-rays, or with a plurality of such pulses.

The technique of Extended X-ray Absorption Fine Structure (EXAFS) spectroscopy is becoming an increasingly important tool for the study of chemical structure in samples which lack long-range order, such as amorphous solids, solutions of biologically important materials, and gases. These studies have gained impetus in recent years by virtue of the availability of synchrotron radiation, which provides a continuous and intense spectrum of the soft X-rays required for EXAFS. A synchrotron, however, is an expensive, cumbersome source of X-rays, to which scientists must travel in order to perform their experiments. A laser X-ray source, on the other hand, is relatively compact, inexpensive, and simple to operate and maintain. Furthermore, there are a variety of novel EXAFS experiments which are inherently beyond the capabilities of synchrotron radiation sources. These experiments, which require short pulse width, intense fluxes of low-energy (<4 keV) X-rays and/or a continuum or a closely packed spectral line structure, are ideally suited to laser-produced X-rays.

The EXAFS spectrum of aluminum has been measured with a nanosecond pulse of soft X-rays generated by a laser-produced plasma. This technique provides a practical alternative to synchrotron radiation for the acquisition of EXAFS data. It also provides a unique capability for the analysis of molecular structure in highly transient chemical species.

BACKGROUND

The problem of determining the identities and exact spatial arrangement of the atoms surrounding any given atom in a molecule is extremely important, and is fundamental to understanding the properties of any type of liquid, gas, or solid. In the case of materials with long range order, such as perfect crystals, this information can often be obtained with X-ray or particle beam diffraction techniques. Such diffraction techniques rely on the fact that all of the atoms in a perfect lattice reside at fixed, periodic distances from any given atom, and that this periodicity is retained regardless of how far one moves within the lattice from the atom in question.

For materials without long range order, the diffraction techniques are far less useful; one can determine local configuration in this way only for relatively simple molecules composed of a single element. Considerable insight or more complicated molecules can often be gained from optical spectroscopy and magnetic resonance techniques. However, these techniques suffer from the drawback of providing only indirect evidence, from which the structural parameters of interest for any given molecule must be inferred.

Many of these limitations can be overcome with the recently developed technique of Extended X-ray Absorption Fine Structure (EXAFS) spectroscopy (1,2). In EXAFS spectroscopy, the X-ray absorption coefficient of a material is measured as a function of energy from the K-edge or L-edge of a specific element in the material to as far as 1000 electron volts above the edge. The absorption of X-rays by the element is accompanied by the ejection of photoelectrons, which can be scattered from neighboring atoms. Back-scattering of these photoelectrons from atoms in the immediate vicinity of the absorbing atom gives rise to a periodic "wiggle" structure in the X-ray absorption spectrum (1,3,4). By analyzing this "wiggle" structure above the absorption edge of a particular element, information can be obtained about the spatial arrangement of atoms in the immediate vicinity of the absorbing species. Since only the nearby atoms are involved, long-range order is not required; therefore, the EXAFS technique can by applied to the study of a broad class of materials, including liquids, gases, and amorphous or crystalline solids.

In the past, chemical structure research with the EXAFS technique has been limited by the lack of suitably intense sources of X-rays. This deficiency is now being remedied to some extent by the increasing availability of synchrotron radiation, which is being harnessed in a number of X-ray test facilities throughout the world. There are certain types of EXAFS experiments, however, which cannot be performed easily with syncrotron X-ray sources. Most significant, perhaps, are those experiments which are designed to analyze highly transient structures such as chemically reactive intermediates or the excited electronic states of molecules. These experiments could be carried out if it were possible to obtain a complete EXAFS spectrum with a single, intense, short pulse of X-rays synchronized with the optical or electrical excitation of the sample. Previous work in our laboratories has indicated that laser-produced plasmas should be nearly ideal X-ray sources for experiments of this type.

Typical apparatus according to the present invention for obtaining EXAFS data of a material comprises means for directing radiant energy from a laser onto a target to produce X-rays of a selected spectrum and intensity at the target, means for directing X-rays from the target onto spectral dispersive means so located as to direct the spectrally resolved X-rays therefrom onto recording means, and means for positioning a sample of material in the optical path of the X-rays. Typically the radiant energy is directed to the target in a single pulse in such manner as to produce soft X-rays from the target suitable for obtaining the EXAFS spectrum of the material, which typically is an element having an atomic number of less than 40.

The apparatus may comprise also means for moving the surface of the target, in which case the radiant energy typically is directed to the moving target surface in a series of pulses in such manner as to produce soft X-rays from the target suitable for obtaining the EXAFS spectrum of the material.

The X-rays from the target preferably comprise continuum radiation in a selected EXAFS spectral regime of the sample. Typically the target comprises essentially an element having a continuum just above the L-lines that includes a selected EXAFS spectral regime of the sample. Or the target may comprise a plurality of elements whose lines are spaced closely enough to form virtually a continuum in a selected EXAFS spectral regime of the sample. Such a target typically comprises a mixture of elements of adjacent atomic numbers.

The radiant energy typically comprises a laser pulse with a power density of at least about $10^{13}$ watts per square centimeter, and the target tyically comprises a solid (typically metal) surface, whereby a surface plasma is formed and raised to the kilovolt temperature regime. The laser pulse preferably is focused to strike a focal spot on the target about 10 to 1000 micrometers in diameter.

The means directing the X-rays from the target typically comprises a baffle having an aperture through which the X-rays can proceed toward the spectral dispersive means, which typically comprises a crystal monochromator. Advantageously the means directing the X-rays from the target directs one portion of them onto the sample of material and an adjacent portion of them alongside the sample.

Typically the recording means comprises a photographic film capable of providing a visible representation of the EXAFS data, and the sample of material comprises a film located in the path of only a portion of the X-rays throughout a selected spectral band so that the X-rays directed onto the photographic film form two separate images thereon comprising a reference spectrum representative of a portion of the X-rays throughout the selected band that was not affected by the sample and an absorption spectrum representative of a portion of the X-rays throughout the selected band that was modified by transmission through the sample.

The spectral dispersive means typically comprises either a Bragg reflector or a diffraction grating, either flat or curved.

The laser pulse typically has a width of less than about 10 nanoseconds; in which case the sample of material may be in a highly transient state, typically comprising a chemically reactive intermediate, molecules with excited electronic states, or other highly transient spatial arrangement of atoms.

DRAWINGS

FIG. 1 is a schematic top view of typical laser-EXAFS apparatus according to the present invention.

FIG. 1A is a schematic perspective view of a portion of the apparatus in FIG. 1, as indicated at A—A therein, showing more definitively the position of the sample in the X-ray beam.

FIG. 2 is a graph showing the laser-EXAFS spectrum of aluminum foil as measured by the apparatus of FIG. 1.

FIG. 3 is a graph of n vs k for aluminum. The points correspond to the features indicated by arrows in FIG. 2.

FIG. 4 is a reproduction of a typical densitometer scan of EXAFS and source spectral data obtained with apparatus as in FIG. 1.

FIG. 5 is a graph similar to FIG. 2 for aluminum film on Mylar, showing the laser-EXAFS spectrum derived from FIG. 4 corrected for background (source).

CARRYING OUT THE INVENTION

It is in fact possible to obtain well-resolved EXAFS spectra of light elements (atomic numbers ranging up to about 40) with a single pulse of soft x-rays produced with neodymium-doped-glass laser. The basic experimental configuration that is used is shown in FIG. 1. In a typical experiment, an infrared laser pulse with an energy of approximately 100 joules and a pulsewidth of approximately 3½ nanoseconds (full-width-half-maximum) is focused onto a solid metal slab target, thereby creating a surface plasma and raising it to the kilovolt temperature regime by means of the inverse bremsstrahlung absorption process. The laser pulse strikes a 100- to 200-micrometer diameter focal spot at an incident intensity of about $10^{14}$ watts/cm$^2$. The resulting x-ray spectrum is dispersed by Bragg reflection from a flat KAP crystal, and recorded on photographic film. The position and range of the recorded spectrum can be varied easily by adjusting the size and position of the dispersing crystal as desired. As the insert in FIG. 1 indicates, the system is so arranged that the thin film sample occupies one-half of the x-ray beam. The reflected (diffracted) x-rays thus form a double image on the photographic film, with the reference portion of the reflected beam striking the top half of the film and the sample portion of the beam striking the lower half of the film. In this way, the entire spectrum is recorded at once, using a single laser pulse. The absorption (EXAFS) spectrum can easily be extracted from the data since both the incident and transmitted x-ray intensities are known for each wavelength.

We have chosen to use film because the need to record the entire spectrum in a few nanoseconds rules out detectors based on the counting of individual photons. Film is the simplest alternative and, when evaluated by digital densitometer techniques, is capable of high resolution and contrast discrimination. With proper choice of film type, grain size, exposure, and data handling, it is possible to obtain results approaching the statistical limit allowed by the incident x-ray photon fluence. Because the photographic film is a nonlinear recording medium, it is necessary to multiply the measured optical densities by a known response factor to determine the absolute x-ray flux at each wavelength. This numerical data handling is done with an on-line minicomputer.

The capabilities of this technique are illustrated by the laser-EXAFS spectrum, shown in FIG. 2, of a thin (2.0 μm) foil of aluminum (7). This spectrum is representative of our results to date and was obtained with the x-rays produced by a single laser pulse incident on an iron slab target. Iron was chosen as the target material because it produced mainly continuum emission in the vicinity of the aluminum K-edge. The same EXAFS spectrum was obtained, however, when the aluminum foil sample was exposed to a pulse of x-rays produced by a copper laser target. This verifies that the results obtained by this technique are independent of the target material, at least for laser targets with relatively smooth x-ray emission in the vicinity of the absorption edge being studied.

The measured spectrum can be interpreted on the basis of the generally accepted formula for EXAFS, which is (1), $$X(k) = (m/4\pi h^2 k) \sum_j (N_j/R_j^2) t_j(2k) \exp(-2R_j/l) \times \sin[2kR_j + 2\delta_j(k)] \exp(-2k^2\sigma_j^2) . \quad (1)$$

Here χ(k) is the fractional modulation of the absorption coefficient due to EXAFS: i.e., $\chi(k)=(\mu-\mu_o)/\mu_o$, where $\mu_o$ is the absorption coefficient for a single atom in a vacuum. The quantity $k=\sqrt{0.262467(E-E_{edge})}$ eV is the photoelectron wave vector in Å$^{-1}$; $N_j$ is the number of atoms scattering at the distance $R_j$; $t_j(2k)$ is the electron scattering matrix in the backward direction for atoms at $R_j$; l is the mean free path of the electron; $\exp(-2\sigma_j^2 k^2)$ is a Debye-Waller factor due to thermal vibrations or static disorder with root-mean-square fluctuations, $\sigma_j$; and sin $[2kR_j 2\delta_j(k)]$ in the sinusoidal interference term, $\delta_j(k)$ being the phase shift. A full analysis of the spectrum on the basis of Equation (1) requires the use of computer-assisted Fourier-transform techniques, as a number of authors have pointed out (1,2). However, it is more illustrative for the present purpose to employ a straightforward graphical technique described by Stern (1) to deduce the nearest neighbor distance. This technique is based on the fact that the EXAFS curve is usually dominated by scattering from the nearest neighbor. This is especially true of the positions of the principal maxima and minima, which are determined mainly by the first sine term in Equation (1), namely:

$$\sin [2kR_1 + 2\delta_1(k)]. \quad (2)$$

If $\delta_1$ is linear in k, then $\delta_1 = \alpha_1 k + \beta_1$, and the argument of the sine term takes the form $2k(R_1 - \alpha_1) + 2\beta_1$. The approximate positions of the maxima and minima of the EXAFS curve are thus given by $$n\pi = 2k(R_1 - \alpha_1) + 2\beta_1, \quad (3)$$

where n = 0,2,4, ... for maxima, and n = 1,3,5, ... for minima. A plot of n versus k for the dominant maxima and minima of the EXAFS spectrum shown in FIG. 2 is given in FIG. 3 with k=0 taken to correspond to the inflection point, $E_{K\text{-}edge} = 1552$ eV, of the measured x-ray absorption coefficient. The points closely fit a straight line with a slope $(2/\pi\chi R_1 - \alpha_1)$ of 1.7 Å. This leads to the basic result $$(R_1 - \alpha_1) \approx 2.6 \text{ Å} \quad (4)$$

Since $R_1 >> \alpha_1$ ($\alpha$HD 1 is typically a few tenths of an angstrom), this result is in good agreement with the known nearest neighbor distance of 2.86 Å for the aluminum face centered cubic lattice(8), and confirms the feasibility of the technique.

The spectrum presented in FIG. 2 is noteworthy for several reasons. In the first place, it serves to illustrate an important feature of the laser-EXAFS technique: The capability to record EXAFS spectra of light elements having absorption edges below about 2 keV which are, at present, difficult to study with other x-ray sources. The laser-EXAFS technique is particularly suitable, at present, for the study of K-edge EXAFS spectra of the elements from carbon to sulfur, and of L-edge EXAFS spectra of elements from sulfur to molybdenum. More importantly, however, the complete laser-EXAFS spectrum presented in FIG. 2 was obtained in only a few nanoseconds, using a single pulse of laser-produced x-rays. This represents a dramatic improvement in the speed and ease of obtaining EXAFS data as compared to all other known x-ray sources. It also makes possible, almost automatically, the measurement of "flash-EXAFS" spectra of transient species having lifetimes as short as a few nanoseconds or less. Experiments along these lines are currently in progress in our laboratory. Thus, we envision that with this technique, it may soon become possible to construct "snapshots" or "movies" of the structural changes which occur in molecules upon excitation by optical or other means. If this proves to be the case, laser-EXAFS will have provided a new and important dimension to the study of chemical structure by x-ray absorption techniques.

Typical apparatus 10 according to the present invention for obtaining EXAFS data of a material 11 comprises means such as a lens 12 for directing radiant energy 13 from a laser 14 onto a target 15 to produce X-rays 16 of a selected spectrum and intensity at the target 15, means such as a baffle 17 for directing X-rays 16 from the target 15 onto spectral dispersive means such as a monochromator 18 so located as to direct the spectrally resolved X-rays 16R therefrom onto recording means such as a photographic film 20, and means such as a support 21 for positioning a sample of material 11 in the optical path 22 of the X-rays 16 and 16R. Typically the radiant energy 13 is directed to the target 15 in a single pulse in such manner as to produce soft X-rays 16 from the target 15 suitable for obtaining the EXAFS spectrum of the material 11, which typically is an element having an atomic number of less than 40.

The apparatus 10 may comprise also means for moving the surface of the target 15 typically in a rotating and advancing motion (not shown) to provide a helical locus of points on a cylindrical surface of the target 15 travelling through the location of a focal spot 23 where the radiant energy 13 strikes the surface. In such a case the radiant energy 13 typically is directed to the moving target surface at 23 in a series of pulses in such manner as to produce soft X-rays 16 from the target 15 suitable for obtaining the EXAFS spectrum of the material 11.

The X-rays from the target 15 preferably comprise continuum radiation in a selected EXAFS spectral regime of the sample 11. Typically the target 15 comprises essentially an element having a continuum just above the L-lines that include a selected EXAFS spectral regime of the sample 11. Or the target 15 may comprise a plurality of elements whose lines are spaced closely enough to form virtually a continuum in a selected EXAFS spectral regime of the sample 11. Such a target 15 typically comprises a mixture of elements of adjacent atomic numbers.

The radiant energy typically comprises a laser pulse 13 with a power density of at least about $10^{13}$ watts per square centimeter, and the target 15 typically comprises a solid (typically metal) surface, whereby a surface plasma is formed and raised to the kilovolt temperature regime. Some EXAFS can be obtained, however, in the ultraviolet and ultrasoft X-ray regime using lower power densities down to about $10^{11}$ watts per square centimeter. The laser pulse 13 preferably is focused to strike a focal spot 23 on the target 15 about 10 to 1000 micrometers in diameter.

The means directing the X-rays from the target typically comprises a baffle 17 having an aperture 24 through which the X-rays 16 can proceed toward the spectral dispersive means 18, which typically comprises a crystal monochromator. Advantageously the means 17 directing the X-rays 16 from the target 15 directs one portion of them 16L (lower in FIG. 1A) onto the sample of material 11 and an adjacent portion of them 16U (upper in FIG. 1A) alongside the sample 11.

Typically the recording means comprises a photographic film 20 capable of providing a visible representation of the EXAFS data, and the sample of material comprises a film 11 located in the path 22 of only a portion of the X-rays (16L in FIG. 1A) throughout a selected spectral band so that the X-rays 16R directed onto the photographic film 20 form two separate images thereon comprising a reference spectrum 26R representative of a portion of the X-rays (16U) throughout the selected band that was not affected by the sample 11 and an absorption spectrum 26A representative of a portion of the X-rays (16L) throughout the selected band that was modified by transmission through the sample 11. Instead of being located as shown in FIGS. 1 and 1A, the piece of material 11 may be located in any other convenient place in the path 22 of the X-rays 16, 16R where it does not intercept the entire cross section of the X-rays in any part of the selected spectral band. Another convenient location for the piece of material 11 is adjacent to the photographic film 20.

The spectral dispersive means 18 typically comprises either a Bragg reflector or a diffraction grating, either flat (as in FIG. 1) or curved in any desired manner (not shown).

The laser pulse typically has a width of less than about 10 nanoseconds; in which case the sample of material 11 may be in a highly transient state, typically comprising a chemically reactive intermediate, molecules with excited electronic states, or other highly transient spatial arrangement of atoms.

References and Notes

1. D. E. Sayers, F. W. Lytle, and E. A. Stern, Adv. X-Ray Anal. 13, 248 (1970); F. W. Lytle, D. E. Sayers, and E. A. Stern, Phys. Rev. B 11, 4825 (1975); E. A. Stern, D. E. Sayers, and F. W. Lytle, ibid., 11, 4836 (1976).
2. P. Eisenberger and B. M. Kincaid, Science 200, 1441 (1978); S. P. Cramer, T. K. Eccles, F. Kutzler, K. O. Hodgson, and S. Doniach, J. Amer. Chem. Soc., 95, 8059 (1976); S. P. Cramer and K. O. Hodgson, Prog. Inorg. Chem., in press.
3. R. de L. Kronig, Z. Phys., 70, 317 (1931); ibid., 75, 191, 468 (1932); H. Peterson, ibid., 98, 569 (1936).
4. C. A. Ashley and S. Doniach, Phys. Rev. 8, 11, 1279 (1975); P. A. Lee and J. B. Pendry, ibid., 11, 2795 (1975).
5. A. Robinson, Science, 190, 1074 (1975); W. Metz and A. Robinson, ibid., 190, 1186 (1975).
6. P. J. Mallozzi, H. M. Epstein, R. G. Jung, D. C. Applebaum, B. P. Fairand, and W. J. Gallagher, in Fundamental and Applied Laser Physics, Proceedings of the Esfahan Symposium, eds., M. S. Feld, A. Javan, and N. A. Kurnit, (Aug. 29–Sept. 5, 1971); P. J. Mallozzi, H. M. Epstein, and R. E. Schwerzel, in Advances in X-Ray Analysis, Proceedings of the 27th Annual Conference on Applications of X-Ray Analysis, eds., G. J. McCarthy, C. S. Barrett, D. E. Leyden, J. B. Newkirk, and C. W. Ruud (Aug. 1–4, 1978). U.S. Pat. No. 4,058,486, Nov. 15, 1977.
7. The aluminum foil was purchased from Reactor Experiments, Inc.
8. L. Pauling, "The Nature of the Chemical Bond," 3rd Edition, Cornell University Press, Ithaca, New York, Chapter 11 (1960).

APPLICABILITY

Structural information is obtained in EXAFS spectroscopy by measuring the absorbance of soft X-rays by the sample of interest. Two types of information may be utilized: the shift of the position of an absorption band edge, and the fine structure of the absorption spectrum.

As an example of the type of structural information which may be derived from EXAFS absorption-edge shift measurements, it has been shown that the "chemical shift" of the absorption edge reflects the "net charge" on an atom; this in turn provides information about the chemical environment of the atom. Measurements of this type (using synchroton-produced X-rays) have been carried out on the molybdenum atom in nitrogenase, a nitrogen-fixing enzyme, so as to determine the chemical state of the molybdenum. By comparing the position of the molybdenum K absorption edge for nitrogenase with the K edge positions of several simple molybdenum compounds, it was inferred that the molybdenum was probably pentacoordinate in the enzyme, with at least one cysteine sulfur ligand. Similar measurements could, in principle, be performed on liquids and gases at any temperature.

Complementary structural information, in the form of the distances from a given atom to its nearest neighbors, is also provided by EXAFS spectroscopy. Because the fine structure near the X-ray absorption edge is caused by back-scattering from the nearest neighbors of the X-ray-absorbing atom, EXAFS spectroscopy can provide detailed structural information which would be difficult or impossible to obtain by other techniques. The powerful advantages of EXAFS spectroscopy are particularly evident in the study of the transition metal atoms which control the behavior of large, biologically-important molecules. EXAFS experiments, utilizing synchroton-produced X-rays, have led to the measurement of the distance between the iron and sulfur atoms in the iron-sulfur protein rubredoxin and the changes in the shape of an iron-porphydrin hemoglobin analog when it becomes bound to molecular oxygen. It has also been suggested that the detailed shape of the EXAFS fine-structure spectrum is sensitive to the identity, as well as the positions, of the back-scattering atoms, making it possible (in principle) to distinguish, for instance, oxygen ligands around a metal atom from nitrogen, sulfur, or carbon.

The importance of the information provided by these X-ray techniques is enormous. By providing insight into the numbers and types of ligand atoms, and their distances from the central metal atom, these techniques permit fundamental knowledge to be derived about the detailed structures of proteins, enzymes, and other molecules of biological significance. The application of these X-ray techniques to chlorophyll, for instance, can help to elucidate the structure of the chlorophyll aggregates which are crucial to the process of photosynthesis in green plants.

A further advantage which is provided automatically by laser-produced X-ray experiments, but which is difficult to obtain with either synchrotron or conventional X-ray sources, is fast time resolution. Because the laser operates in very brief pulses, on the order of a nanosecond long, the X-ray pulse has similar time resolution. This means that a laser-produced X-ray experiment can detect and measure the changes in the structure of a molecule when it absorbs light and then decays from an excited state to the ground state. Many other types of fast kinetic experiments can be envisioned. Such measurements would have immediate impact on many aspects of spectroscopy and photochemistry. The techniques can be adapted to such diverse samples as natural biological membranes, liquid solutions, and flowing gases, making possible the study of a wide variety of samples. The potential benefits to be gained from the further development of laser-produced X-ray spectroscopy are clearly significant and far-reaching.

Typically the target 15 comprises a metal or other solid material, but it may comprise a material in the liquid state, such as a stationary pool, or a stream or droplets of liquid moving into and past the focal spot 23 at the proper time or times. Although the recording means 20 typically comprises a photographic film, other detectors could be used, such as arrays of charge coupled detectors, silicon diodes, or vidicon phototubes.

FURTHER DETAILS

Conceptually, the EXAFS wiggle mentioned earlier is caused in the following manner. The wave function of the photoelectron (the final state of the X-ray absorption transition) consists of an outgoing part and a scattered part, which overlap near the origin, where the wave function of the initial (bound) state of the electron is concentrated. The overlap produces an interference which is either constructive or destructive, depending on the wave number $k = 2\pi/\lambda = 1/\hbar \sqrt{2m(E-E_{edge})}$ of the photoelectron. When the interference is constructive, the increased amplitude near the origin results in an enhanced absorption coefficient. When the interference is destructive, the absorption coefficient is diminished. Thus, when the relative phase relationship between the outgoing and incoming photoelectrons is changed by varying the photon energy of the incident X-rays, a periodic modulation in the absorption coefficient results. The modulation can be interpreted on the basis that each atom (or shell of atoms) surrounding the absorbing atom will contribute a single modulated sine wave in k to the absorption coefficient.

Aside from the laser and beam focusing apparatus, which have already been discussed, the basic experimental apparatus consists of a modified General Electric XRD-7 vacuum spectrometer with the X-ray tube replaced by a laser-plasma X-ray source. The target is mounted on a remotely controlled XYZ translation stage to permit a change of targets or target position in the vacuum. The crystal angle is also remotely controlled and can be adjusted in the vacuum.

The iron target used to produce the aluminum EXAFS spectrum emits both continuum and line radiation. The lines above $h\nu = 1$ keV are bunched into a L-group, which lie mostly below 1.5 keV, and a K-group, which lie above about 5 keV. The region between 1.5 keV and 5 keV is mostly continuum radiation with a characteristic plasma bremsstrahlung temperature of approximately 800 eV. For the purpose of planning experiments, the following formula for the continuum radiation between 1.5 keV and 5 keV generated by a 100 joule laser pulse incident on an iron slab target has proved useful:

$$I(h\nu) = 0.25/2\pi R^2 \exp(-h\nu/800) \text{ J/eV/cm}^2 \qquad (5)$$

where R is the distance from the source to the observer and $h\nu$ is the photon energy in eV. Thus, the K-edge of Aluminum ($E_K = 1560$ eV) lies in the most intense portion of the iron continuum, just above the iron L-group. This method of matching target with sample seems reasonable when studying X-ray edges in the 1-2 keV regime: e.g., when studying K-edges of elements with atomic numbers $Z \simeq 10-20$ and L-edges of elements with atomic numbers $Z \simeq 30-40$. It appears that the appropriate targets for such studies have atomic numbers in the range $Z \simeq 20-30$.

The crystal that was used in the experiments was 1 centimeter wide and 2.5 centimeters long, and was located approximately 10 centimeters from the source. The X-rays are reflected according to the formula $2d \sin \theta = m\lambda$, where $\theta$ is the Bragg angle: i.e., the angle of incidence measured with respect to the crystal plane. Since the 2d spacing of KAP is 26.64 A, $\theta \simeq 17°$ for first order reflection (m=1) of X-rays at the K-edge of the Aluminum sample. The rocking-curve width (i.e., the full width at half maximum of the intensity versus angle profile for monochromatic X-rays) of the crystal at this angle is $1.2 \times 10^{-4}$ radians, corresponding to an energy spread $\Delta h\nu \simeq 0.62$ electron volts. The reflection efficiency at the peak of the rocking-curve at this angle is about 5 percent.

The data given above may be used to calculate the number of photons per electron volt that strike the film. This quantity can be used to evaluate the sensitivity with which the X-ray absorption coefficient can be measured. A convenient starting point is Equation (5), which tells us that the X-ray fluence directed at the crystal at 10 centimeters, in the vicinity of the K-edge, is $$.025 \times e^{-\frac{1560}{800}} \times \frac{1}{2\pi \times 10^2} = 5.7 \times 10^{-6} \text{ J/eV/cm}^2, \text{ or}$$

$$(5.7 \times 10^{-6}) \times (6 \times 10^{18}) \times 1/1560 = 2.2 \times 10^{10} \text{photons/eV/cm}^2.$$

The number of photons reflected from the 1 centimeter wide KAP crystal is therefore $(2.2 \times 10^{10}) \times 10 \times (1.2 \times 10^{-4}) \times 0.05 = 1.3 \times 10^6$ photons/eV. This figure ignores attenuation through the sample, which is approximately 2 X-ray mean-free-paths thick. What really matters in determining the sensitivity of the absorption coefficient measurement is the number of photons that strike the film after passage through the sample. This is $(1.3 \times 10^6) \times (1/e^2) \simeq 2 \times 10^5$ photons/eV. In analyzing the data, the energy spectrum was divided into 5 eV energy intervals. There are therefore approximately $10^6$ photons in each energy interval, which in principle allows an interval-to-interval contrast of $\Delta N/N = 1/N^{\frac{1}{2}} \simeq 10^{-3}$, or approximately 0.1 percent. The reasons that a sample thickness of 2 mean-free-paths is used is that it omptimizes the contrast obtainable with a given sized energy interval. Two mean-free-paths also optimizes the energy resolution obtainable at a given contrast level.

The photographic film used to record the Aluminum EXAFS spectrum shown in FIG. 4 is Kodak NS-2T. This film was chosen because, under the particular conditions of that experiment, the data is produced in the "linear" range of the film, where the optical density is proportional to the log of the exposure. In order to minimize the effect of film nonlinearity, the "reference" portion of the X-ray beam reflected from the crystal is passed through a thin layer of mylar whose thickness is adjusted to produce the same average exposure as the "sample" portion of the beam. Analysis of the film record is performed automatically with a Video Digitizer, serving as a computerized densitometer. The wavelength calibration of the film record is accomplished by noting where well-known X-ray lines generated by focusing the laser beam onto selected targets lie, and interpolating between them.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

I claim:

1. Apparatus for obtaining EXAFS data of a material, comprising means for directing radiant energy from a laser onto a target in such manner as to produce X-rays at the target of a selected spectrum and intensity, suitable for obtaining the EXAFS spectrum of the material, means for directing X-rays from the target onto spectral dispersive means so located as to direct the spectrally resolved X-rays therefrom onto recording means, and means for positioning a sample of material in the optical path of the X-rays, the recording means providing a reference spectrum of X-rays not affected by the sample and an absorption spectrum of X-rays modified by transmission through the sample.

2. Apparatus as in claim 1, wherein the radiant energy is directed to the target in a single pulse in such manner as to produce soft X-rays from the target.

3. Apparatus as in claim 1, comprising also means for moving the surface of the target, wherein the radiant energy is directed to the moving target surface in a series of pulses in such manner as to produce soft X-rays from the target.

4. Apparatus as in claim 1, wherein the X-rays from the target comprise continuum radiation in a selected EXAFS spectral regime of the sample.

5. Apparatus as in claim 1, wherein the target comprises essentially an element having a continuum just above the L-lines that includes a selected EXAFS spectral regime of the sample.

6. Apparatus as in claim 1, wherein the target comprises a plurality of elements whose lines are spaced closely enough to form virtually a continuum in a selected EXAFS spectral regime of the sample.

7. Apparatus as in claim 6, wherein the target comprises a mixture of elements of adjacent atomic numbers.

8. Apparatus as in claim 1, wherein the material is an element having an atomic number of less than 40.

9. Apparatus as in claim 1, wherein the radiant energy comprises a laser pulse with a power density of at least about $10^{13}$ watts per square centimeter, and the target comprises a solid surface, whereby a surface plasma is formed and raised to the kilovolt temperature regime.

10. Apparatus as in claim 9, wherein the laser pulse is focused to strike a focal spot on the target about 10 to 1000 micrometers in diameter.

11. Apparatus as in claim 1, wherein the means directing the X-rays from the target comprises a baffle having an aperture through which the X-rays can proceed toward the spectral dispersive means.

12. Apparatus as in claim 1, wherein the spectral dispersive means comprises a crystal monochromator.

13. Apparatus as in claim 1, wherein the means directing the X-rays from the target directs one portion of them onto the sample of material and an adjacent portion of them alongside the sample.

14. Apparatus as in claim 1, wherein the recording means comprises a photographic film capable of providing a visible representation of the EXAFS data.

15. Apparatus as in claim 14, wherein the sample of material comprises a film located in the path of only a portion of the X-rays throughout a selected spectral band so that the X-rays directed onto the photographic film form two separate images thereon comprising a reference spectrum representative of a portion of the X-rays throughout the selected band that was not affected by the sample and an absorption spectrum representative of a portion of the X-rays throughout the selected band that was modified by transmission through the sample.

16. Apparatus as in claim 1, wherein the spectral dispersive means comprises a Bragg reflector.

17. Apparatus as in claim 1, wherein the spectral dispersive means comprises a diffraction grating.

18. Apparatus as in claim 2, wherein the laser pulse has a width of less than about 10 nanoseconds.

19. Apparatus as in claim 18, wherein the sample of material is in a highly transient state.

20. Apparatus as in claim 18, wherein the sample of material comprises a chemically reactive intermediate, molecules with excited electronic states, or other highly transient spatial arrangement of atoms.

* * * * *